(12) United States Patent
Kriksunov et al.

(10) Patent No.: US 8,196,576 B2
(45) Date of Patent: Jun. 12, 2012

(54) INHALER

(75) Inventors: Leo B Kriksunov, Princeton, NJ (US); Anand V Gumaste, West Windsor, NJ (US)

(73) Assignee: Microdose Therapeutx, Inc., Monmouth Junction, NJ (US)

( * ) Notice: Subject to any disclaimer, the term of this patent is extended or adjusted under 35 U.S.C. 154(b) by 1314 days.

(21) Appl. No.: 11/680,084

(22) Filed: Feb. 28, 2007

(65) Prior Publication Data

US 2008/0202514 A1 Aug. 28, 2008

(51) Int. Cl.
*B65D 83/06* (2006.01)
*A61M 16/10* (2006.01)

(52) U.S. Cl. .................. 128/203.15; 128/203.12

(58) Field of Classification Search ............. 128/205.21, 128/200.14, 200.16, 200.18, 200.21, 200.24, 128/203.12–203.15, 203.19, 203.21, 203.25, 128/203.27, 204.14, 204.21; 239/4, 102.1, 239/329, 338, 419.5; 222/58, 61, 161, 196, 222/199, 344, 358, 361–362, 409, 485

See application file for complete search history.

(56) References Cited

U.S. PATENT DOCUMENTS

| | | | | |
|---|---|---|---|---|
| 4,094,317 A | * | 6/1978 | Wasnich | 128/200.16 |
| 5,152,284 A | * | 10/1992 | Valentini et al. | 128/203.21 |
| 5,727,546 A | * | 3/1998 | Clarke et al. | 128/203.15 |
| 5,908,158 A | * | 6/1999 | Cheiman | 239/102.2 |
| 6,840,239 B2 | | 1/2005 | Myrman | |
| 2002/0078947 A1 | * | 6/2002 | Gumaste | 128/200.14 |
| 2003/0192539 A1 | | 10/2003 | Myrman | 128/203.15 |
| 2003/0192540 A1 | * | 10/2003 | Myrman et al. | 128/203.15 |
| 2004/0263567 A1 | * | 12/2004 | Hess et al. | 347/47 |
| 2005/0087189 A1 | | 4/2005 | Crockford et al. | |
| 2005/0109659 A1 | * | 5/2005 | Hickey et al. | 206/538 |
| 2005/0172962 A1 | | 8/2005 | Gumaste et al. | |
| 2006/0174869 A1 | | 8/2006 | Gumaste et al. | 128/200.14 |
| 2007/0119969 A1 | * | 5/2007 | Collins et al. | 239/102.1 |
| 2008/0289629 A1 | * | 11/2008 | Djupesland et al. | 128/203.15 |

FOREIGN PATENT DOCUMENTS

UA 27570 7/1994

OTHER PUBLICATIONS

Chinese Official Action and translation dated Sep. 14, 2011 issued in related application serial No. 200880006600.1 (8 pgs).
New Zealand Examination Report issued in Appln. No. 579264, dated Feb. 21, 2011 (2 pgs).
Israeli Office Action issued in Appln. No. 200565, dated May 23, 2011 (1 pg).
European Official Action dated Aug. 11, 2011 in Appln. No. 08 743 607.7-2320, (4 pgs).
Hungarian Search Report and Written Opinion issued in Appln. No. 2009055799, dated Jul. 15, 2010 (8 pgs).
Russian Official Action and translation dated Jan. 23, 2012 issued in related application serial No. 2009135772/14(050476) (6 pages).

* cited by examiner

*Primary Examiner* — Justine Yu
*Assistant Examiner* — Rachel Young
(74) *Attorney, Agent, or Firm* — Hayes Soloway P.C.

(57) ABSTRACT

A dry powder inhaler has a vibrator coupled to a blister filled with a dry powder drug substance. One or more of drug ejection apertures in the blister are substantially opposite the vibrator. One or more air intake apertures in the blister are not opposite the vibrator. Upon vibration of the vibrator, the drug substance is deaggregated, aerosolized, and ejected from the drug ejection apertures for inhalation by a patient.

19 Claims, 10 Drawing Sheets

INHALER

FIELD OF THE INVENTION

Embodiments of this invention are related to medical devices and drug delivery devices, specifically to delivery of aerosolized drugs, to inhalation of drugs for delivery to lungs and gastrointestinal tract, and to intranasal drug delivery.

BACKGROUND OF THE INVENTION

Devices for delivery of aerosolized drug substances, including delivery via inhalation, are known in the art, examples including U.S. Pat. Nos. 5,694,920, 6,026,809, 6,142,146, all by Abrams and Gumaste, U.S. Pat. No. 3,948, 264 by Wilke et al., U.S. Pat. No. 6,971,383 by Hickey et al., U.S. Pat. No. 7,117,867 by Cox et al., U.S. Pat. No. 6,901,929 by Burr et al., U.S. Pat. No. 6,779,520 by Genova et al., U.S. Pat. No. 6,748,944 by DellaVecchia et al., U.S. Pat. No. 5,590,645 by Davies et al. The above patents also provide an overview of various aerosolization and inhalation devices and techniques.

A range of aerosolization and inhalation drug delivery devices is known, including metered dose inhalers, nebulizers, dry powder inhalers, thermal vaporizers, and other systems, with differences related to methods and efficiency of aerosolization and delivery of drug substances to the patient. Metered dose inhalers are typically using pressurized gas to aerosolize the drug substance. Disadvantages of these inhalers are related to difficulties to control the delivered dose of the drug substance and also to high speed of aerosol particles, resulting in particles impinging and depositing on various surfaces in the mouth and in the throat of a patient. Inhalation devices delivering drug substances as a dry powder are known as dry powder inhalers. Passive dry powder inhalers rely on the patient's inspiratory effort to de-aggregate and aerosolize drug substance for inhalation, while active dry powder inhalers typically input additional energy, such as mechanical or electrical energy in order to improve the efficiency of powder deaggregation and aerosolization, to decrease the inspiratory effort needed from the patient, and to achieve better inspiratory flow independence of the inhaler performance. Typically for delivery of drug substances to the lungs of a patient via inhalation, the drug aerosol particle size has to be less than about 10 microns, more preferably less than about 6 microns, and for delivery to deep lung less than about 3.3 microns. Larger size particles will be delivered to the mouth and throat of the patient and as a result will be delivered to the gastrointestinal tract of the patient. There is a need to increase the quantities of a drug that dry powder inhalers are capable of aerosolizing during a single inhalation by a patient, e.g. within one to three-four seconds. There is also a need to increase the speed of deaggregation and aerosolization of powders by dry powder inhalers.

Dry powder inhalation devices described in U.S. Pat. Nos. 5,694,920, 6,026,809, 6,142,146, all by Abrams and Gumaste, utilize vibratory means to deaggregate and aerosolize dry powder medication for delivery to the patient as an aerosol. US Patent Publication 2005/0183724 by Gumaste and Bowers discloses a synthetic jet-based medicament delivery method and apparatus.

BRIEF DESCRIPTION OF THE INVENTION

Briefly, an embodiment of the invention comprises a device for inhalation of aerosolized drug substances, wherein a high frequency vibrator is coupled to a container filled with a dry powder drug substance. Vibrations of the vibrator result in deaggregating, aerosolizing and ejecting of the drug substance from the container for inhalation by a patient. One or more apertures in the container are substantially opposite the vibrator and are used primarily for drug ejection, via synthetic jetting or other mechanisms of ejecting the powder from the container. At least one other aperture in the container is used primarily for ingress of outside gas or air into the container.

Unexpected results, as illustrated in the examples to follow, were obtained when performing experimental testing of the embodiments of the present invention for use as an inhalation and/or aerosolization device, with observations of substantially faster aerosolization and ejection of dry powders, as well as capability of aerosolizing substantially larger quantities of dry powders vs. prior art.

BRIEF DESCRIPTION OF THE DRAWINGS

In the drawings, like numerals refer to like parts or features throughout the several views.

DETAILED DESCRIPTION OF THE PREFERRED EMBODIMENTS OF THE INVENTION

Figure 1:
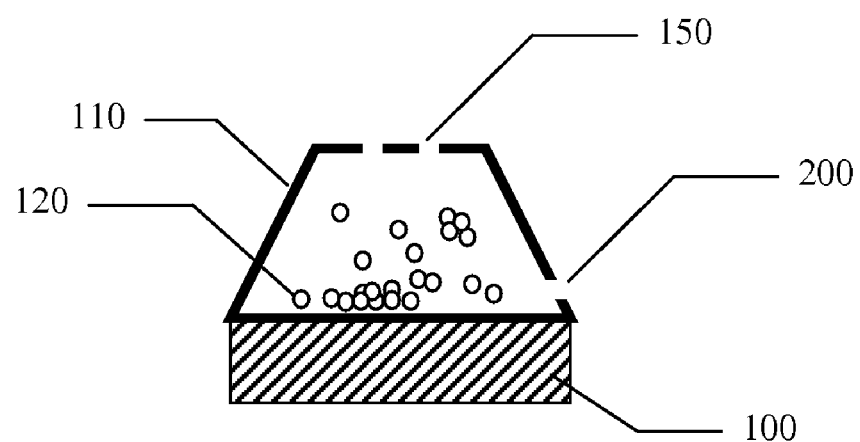
FIG. 1 is a cross-sectional view of an embodiment of the present invention showing a container with a drug substance coupled to a vibrator.
Figure 2:
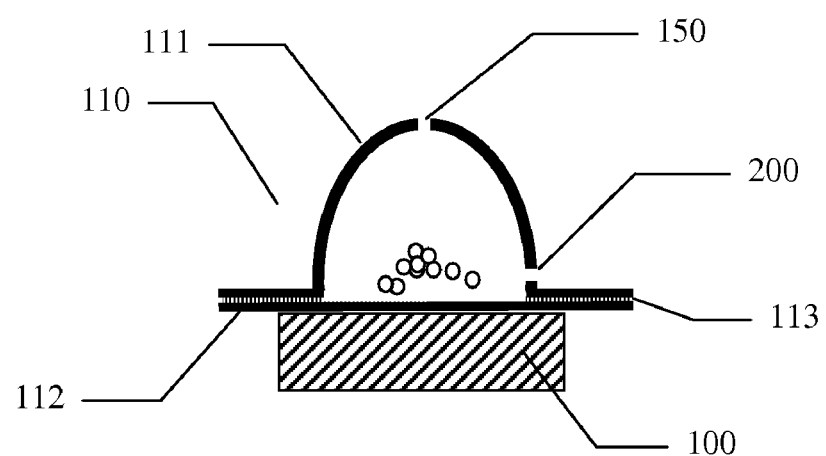
FIG. 2 is a cross-sectional view of an embodiment of the present invention showing a container with a drug substance coupled to a vibrator.

A cross-sectional view of an embodiment of the present invention is schematically illustrated in FIG. 1. A vibrator 100 is coupled to a blister or container 110 which contains a drug substance or substances 120. Vibrator 100 can be a piezo actuator or piezo transducer, or a mechanical vibrator, an electromagnetic vibrator, a magnetostrictive element, or other vibrating mechanism, as known in the art. In one embodiment, a piezo actuator is utilized, typically consisting of a piezo ceramic element and a metallic body, of either unimorph or bimorph design. Piezo actuator designs known in the art can be used, including, but not limited to, air transducers and piezo-electric sensing elements. Additionally, polymeric piezo materials and actuators based on polymeric piezo materials can be utilized as vibrators. Vibrators based on piezo actuators are energized, as known in the art, by supplying electric power, typically alternating electric current of appropriate frequencies and amplitude, to the piezo component. Piezo actuators tuned to various resonant frequencies can be used, for example with resonant frequencies in the range from about 1 kHz to about 100 kHz, more typically in the ultrasonic range from about 30 kHz to about 45 kHz, and amplitude of mechanical oscillations from about 1 micron to about 50 microns peak to peak. Vibrator 100 is capable of vibrating, with either fixed or variable frequency, or several frequencies simultaneously, and to transmit the vibratory movement to the container 110. The frequency of vibration can range from less than 1 Hz to hundreds kHz, more typically the vibration frequency is from about 25 kHz to about 50 kHz. In the embodiment shown in FIG. 1, vibrator 100 is in direct contact with container 110 and thus is directly coupled to container 110.

Container 110 has at least one drug ejection aperture 150 substantially opposite vibrator 100 and serving primarily for ejection of drug substance 120. However, outside air or gas can also enter container through apertures 150. Further, container 110 has at least one side wall aperture 200 which is not substantially opposite to vibrator 100. Side wall aperture 200 is not used for ejection of drug substance but permits air or gas to enter container 110 from outside and thus facilitates deaggregation, aerosolization, and ejection of drug substance 120 from container 110 via drug ejection apertures 150.

Drug substance or substances 120 are provided as a dry powder, but other forms of drug substance are possible, such as liquid or gas. A single component drug substance (neat drug) can be used, as well several drug substances, or drug substances combined with excipients, such as lactose, or combinations thereof. Other additives, such as pharmaceutically inactive ingredients, de-aggregation agents, etc. can also be added to the pharmaceutically active drug substance or substances.

Container 110 is made of metal, plastic, or composite materials. In one embodiment of the present invention, container 110 is a blister pack made of cold formed or thermoformed film, with film materials being polymer, metallic foil, multi-layer polymer-metallic foil clad films, and barrier coated metallic or polymeric films. In an embodiment of the present invention illustrated in FIG. 2, container 110 is a single use blister pack comprising generally conical, pyramidal, semi-spherical, elliptical, or similar top part 111 and flat bottom part 112, wherein top part 111 and bottom part 112 are hermetically sealed to each other by methods known in the art, including but not limited to bonding, thermal sealing, pressure sealing, ultrasonic sealing, and the like. Area of bonding or sealing 113 is also schematically shown in FIG. 2 in the area of contact between the top part 111 and the bottom part 112. Vibrator 100 is shown in direct contact with flat bottom part 112 of container 110.

A number of possible shapes and forms of blister pack or container 110 are schematically shown in FIGS. 3A through 3F, including flat top conical shapes (FIGS. 3A, 3D, 3G); cylindrical shapes (FIGS. 3B and 3E), which is also shown in FIG. 4; and semi-spherical or conical shapes (FIGS. 3C, 3F, 3H).

The dimensions of container 110 in one embodiment are from about 1 mm to about 30 mm in diameter, and from about 1 mm to about 30 mm in height, however larger or smaller containers 110 can be utilized according to this invention. In another embodiment, the diameter of container 110 is from about 3 to about 12 mm, while the height of container 110 is from about 3 to about 12 mm.

The dimensions of drug ejection apertures 150 are from about 10 microns to about 1000 microns, with preferred dimensions from about 50 microns to about 500 microns. Dimensions of side wall apertures 200 are from about 1 micron to about 1000 microns, with preferred dimensions from about 25 microns to about 500 microns. In one embodiment of the present invention, the total area (cross section) of all drug ejection apertures 150 is at least two or more times the total area (cross section) of all side wall apertures 200. In another embodiment of the present invention, the total area (cross section) of all drug ejection apertures 150 is at least five times the total area (cross section) of all side wall apertures 200.

The number of drug ejection apertures 150 is from 1 to about 10, with number of drug ejection apertures 150 in another embodiment being from about 3 to about 6. The number of side wall apertures 200 is from 1 to about 10, with number of side wall apertures 200 in another embodiment being from 1 to 2.

In one embodiment of the present invention, vibrator 100 is directly coupled to container 110 and has substantially the same dimensions as the dimensions of the container 110 on the coupling surfaces, so that the areas of coupling of corresponding surfaces of vibrator 100 and container 110 are substantially the same, as shown in FIGS. 1, 3B, 3C, 3D, 3E, 3H, and FIG. 4. In another embodiment of the present invention, shown in FIGS. 2, 3A, 3F, and 3G, dimensions of vibrator 100 are larger or smaller vs. dimensions of the container 110 on the coupling surfaces. Referring now to the embodiments of the present invention shown in FIG. 5, vibrator 100 can also be coupled to container 110 via a mechanical spacer or integral pin 130, as shown in FIG. 5A, or through an air gap 140, as shown in FIG. 5B. Vibrator 100 can also be coupled to container 110 from a side of the container 110 (embodiment not shown). Vibrator 100 can also be disposed directly or partially inside of container 110 (embodiment not shown).

The directionality of drug ejection apertures 150 shown in FIGS. 1, 2, 3A through 3F, 4, and 5 is substantially normal or perpendicular to the top surface of vibrator 100, or to the plane of coupling between vibrator 100 and container 110, while the directionality of side wall apertures 200 is substantially parallel to top surface of vibrator 100, or to the plane of coupling between vibrator 100 and container 110. However other directionality of apertures 150 and 200 can be used, as shown in FIGS. 3G and 3H, wherein drug ejection apertures 150 are not normal or perpendicular to the top surface of vibrator 100, or to the plane of coupling between vibrator 100 and container 110, and side wall apertures 200 are not substantially parallel to top surface of vibrator 100, or to the plane of coupling between vibrator 100 and container 110.

In operation of an embodiment of the present invention, upon actuation of vibrator 100 and initiation of vibrations, vibration energy is transferred to container 110 whereas drug substance is ejected from container 110 though at least one drug ejection aperture 150. In one embodiment of the invention, a synthetic jet of fluid, which can be gas or gas/drug substance mixture, is established through the drug ejection aperture 150. Synthetic jet is characterized in that the fluid is moving in both directions through aperture 150 with simultaneous formation of vortices on both sides of the aperture. Synthetic jetting of gas or liquid is known to these skilled in the art and is characterized by high speed jets of gas or other fluid emanating from an orifice in an enclosed chamber, with fluid entering and exiting the chamber multiple times through an orifice, so that fluid expelled from the chamber is replenished by fluid entering the chamber from outside. Reference is made to US Patent Publication 2005/0183724 by Gumaste and Bowers which describes synthetic jets. Due to gas moving through an orifice in both directions, synthetic jets can continue indefinitely. Forming synthetic jets may require establishment of acoustic waves which can be established, for example, by piezo-vibrators, and may require a combination of specific parameters, including frequencies, orifice dimensions, and container shape and dimensions for establishment of strong, sustained, and reproducible synthetic jets.

Figure 6:
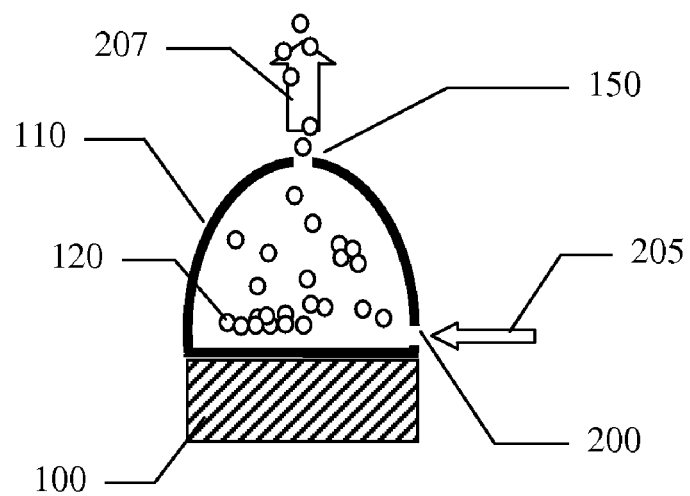
FIG. 6 is a cross-sectional view of an embodiment of the present invention showing a container with a drug substance coupled to a vibrator.

Referring now to FIG. 6, an embodiment of the present invention in operation is shown, wherein upon actuation of vibrator 100, side wall aperture 200 permits outside air or gas to enter container 110 (as schematically shown by arrow 205) and thus facilitates efficient ejection of drug substance 120 from drug ejection aperture 150 (as schematically shown by arrow 207), increasing speed of ejection and quantities of drug substances capable of being ejected from container 110.

Figure 7:
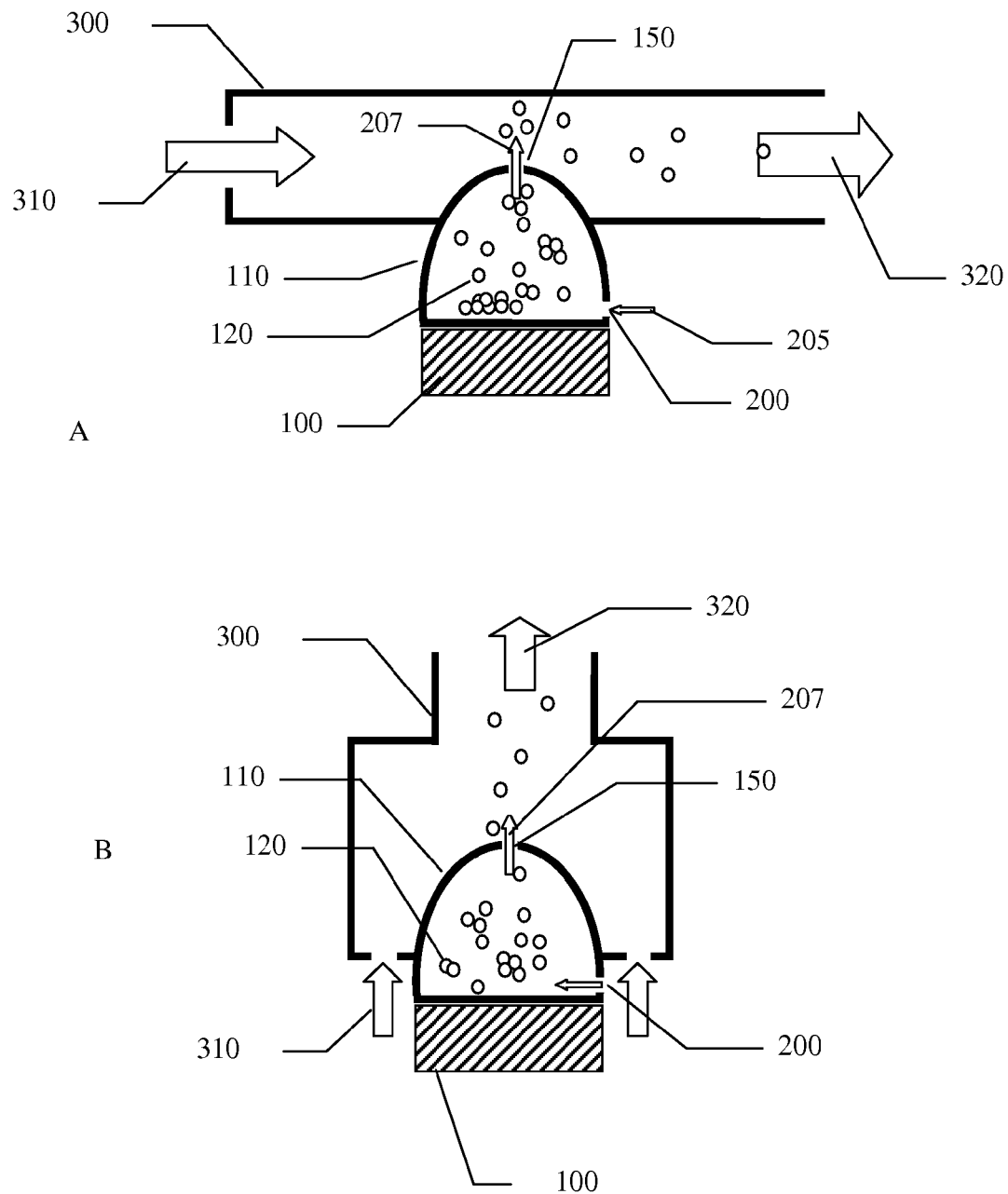
FIG. 7 is a cross-sectional view of embodiments of the present invention showing inhalation devices.

Referring now to FIG. 7, an embodiment of the present invention is shown as a schematic representation of a dry powder inhaler, comprising container 110, vibrator 100, and a flow channel 300. Flow channel 300 shown in FIG. 7A is of the cross-flow type, whereby air is flowing generally perpendicularly to the direction of drug substance 120 ejection from container 110, said direction of the ejection is indicated by arrow 207. The flow channel 300 shown in FIG. 7B is of the parallel-flow type, whereby air is flowing generally parallel to the direction of drug substance 120 ejection from container 110, with the direction of the ejection indicated by arrow 207. A range of intermediate arrangements of the flow channel 300 and the container 110 are possible, whereby air is moving in a more complex pathway intermediate between parallel flow and cross-flow (embodiment not shown). Upon inhalation by the patient, the air is flowing through the flow channel 300, with air entering as shown by arrows 310 and exiting the device for inhalation as shown by arrows 320.

Upon actuation of vibrator 100, drug substance 120 is deaggregated, aerosolized, and ejected from the container 110 through drug ejection aperture 150. The sequence of the deaggregation, aerosolization, and ejection of drug substance 120 is not necessarily proceeding in the above order, wherein all three processes can be occurring simultaneously, or consecutively in any order depending on the parameters of the process, with the end result being drug substance 120 ejected from container 110 through drug ejection aperture 150, and aerosolized drug substance 120 appearing inside flow channel 300. Aerosol of the drug substance 120 is then being picked up by stream of air 310 outside of container 110, resulting in drug substance 120 being delivered to the inhaling patient as shown by arrow 320. The ingress of outside air through side wall aperture 200, as shown by arrow 205, facilitates process of deaggregation, aerosolization, and ejection of drug substance 120 through drug ejection apertures 150.

Figure 8:
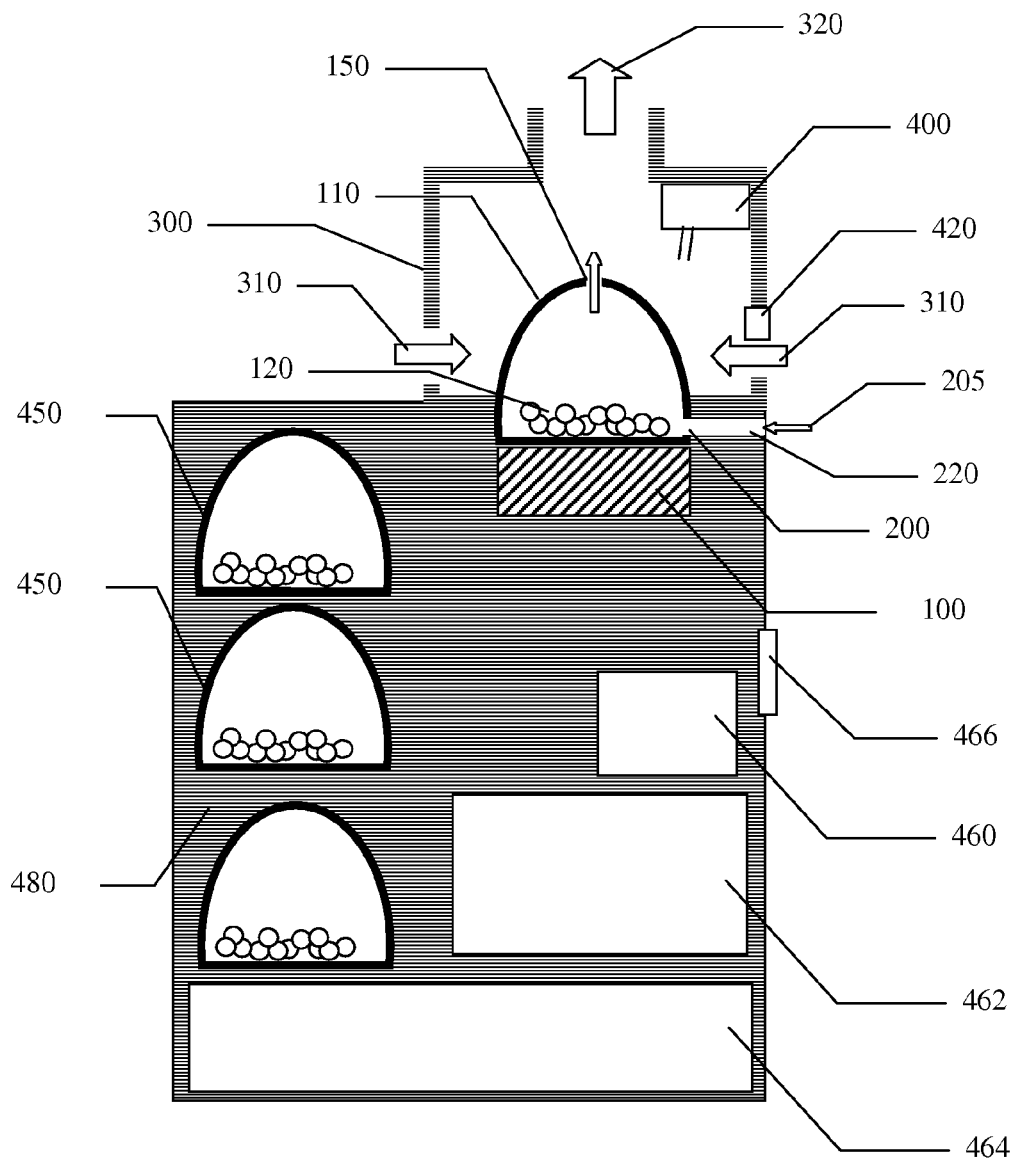
FIG. 8 is a cross-sectional view of an embodiment of the present invention showing an inhalation device.

Referring now to FIG. 8, an embodiment of the present invention is shown as a schematic of a dry powder inhaler with an inhaler body 480, wherein within and also outside of inhaler body 480 are disposed several of the inhaler components, including container 110; vibrator 100; flow channel 300; electronic board and circuitry 462 serving to electrically drive vibrator 100 and other electronic components of the inhaler. Battery 464 is serving for energizing electronic components and vibrator, said battery can be any energy source such as battery pack, which can be a primary or rechargeable battery, or a fuel cell. Other optional components of inhaler shown in FIG. 8 are piercing means 400, for piercing drug ejection apertures and or side wall apertures in container or blister 110; additional single dose drug containers 450; sensor 420 for sensing and detecting inspiration by a user or patient, adapted to detect inspiratory air flow by a user as shown by arrows 310 and interconnected to electronic circuit 462 to activate vibrator 100 and drug ejection and aerosolization process. Sensor 420 is preferably capable, together with electronic board and circuitry 462 of detecting presence and strength of air flow in the inhaler and optionally the directionality of air flow. Patient feedback devices 460 and 466 are providing sensory feedback to the patient as well as optional dose counters and indication displays indicating to the user the status of the drug delivery and various options. Arrow 320 shows air being inhaled by the patient. Channel 220 provides access of outside air to side wall aperture 200 so that upon actuation of vibrator 100 outside air can enter container 110 as shown by arrow 205.

Figure 9:
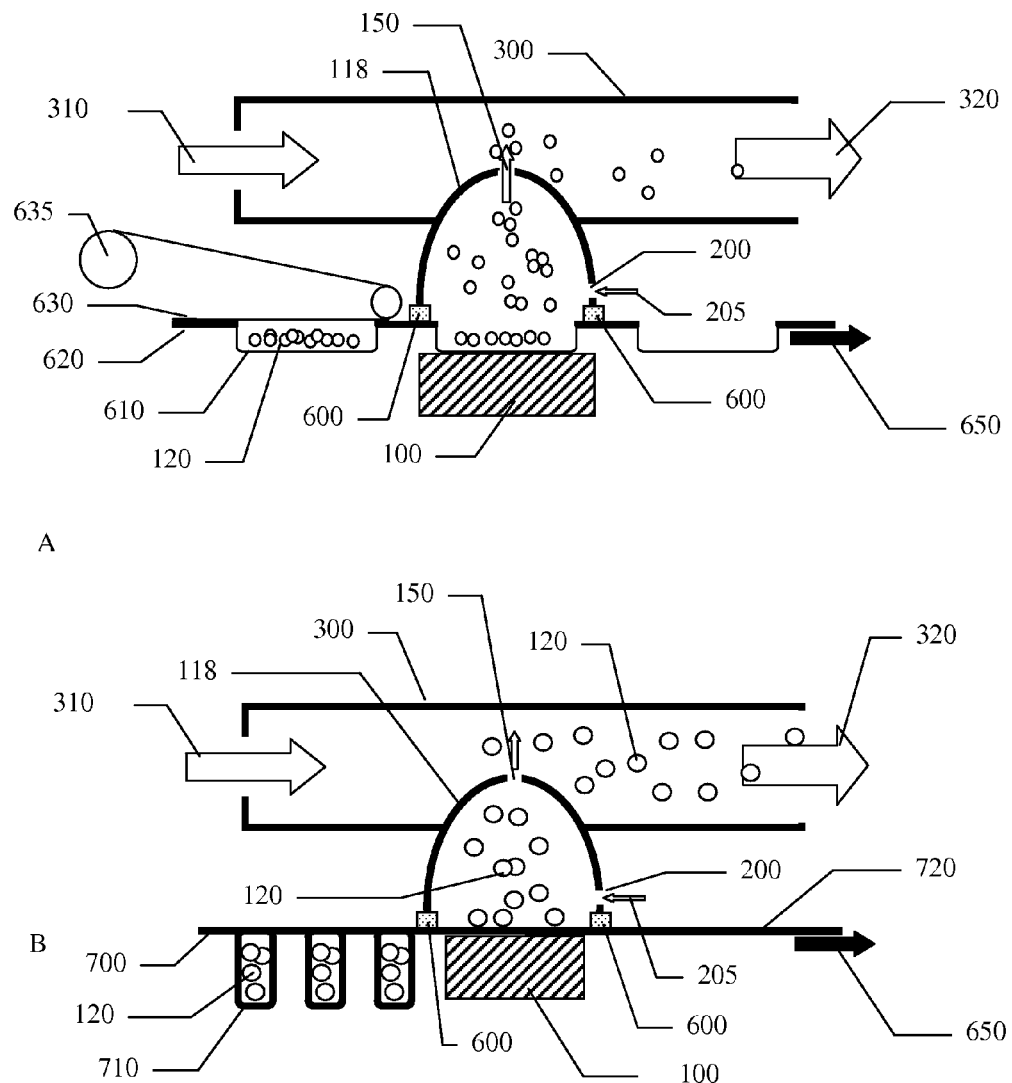
FIG. 9 is a cross-sectional view of embodiments of the present invention showing inhalation devices.

Referring now to FIG. 9, embodiments of the present invention are shown as schematic representation of dry powder inhalers with a multi-use container 118, wherein drug substance 120 is provided in single use drug packs 610 and 710 arranged on a carrier tape 620 and 700. The direction of tape movement is shown by arrow 650. In the embodiment shown in FIG. 9A, single use drug packs 610 are covered with a lidding tape 630 which is collected on a spool 635, thus exposing drug substance 120 for ejection via drug ejection apertures 150. In another embodiment (not shown), lidding tape 630 is not removed from single use drug packs 610 but is perforated before or upon entering multi-use container 118, thus exposing drug substance 120 for ejection via drug ejection apertures 150. Multi-use container 118 is in contact with carrier tape 620 through compressible gasket or O-ring 600. Upon inhalation by the patient, vibrator 100 is actuated, thus ejecting drug substance 120 through ejection apertures 150. Outside air enters container 118 as shown by arrow 205 via side wall aperture 200, while aerosolized drug substance being inhaled by the patient as shown by arrow 320 and air incoming into flow channel 300 is shown by arrow 310.

Similarly, in FIG. 9B, drug substance 120 is provided in single use drug packs 710 comprising pockets of tape folded on itself, arranged on a carrier tape 700. The direction of tape movement is shown by arrow 650. Pulling carrier tape 700 results in opening of pockets of tape 710 under multi-use container 118, with multi-use container 118 in contact with carrier tape 700 through compressible gasket or O-ring 600. Upon inhalation by the patient, vibrator 100 is actuated, thus ejecting drug substance 120 through ejection aperture 150. Outside air enters container 118 as shown by arrow 205 via side wall aperture 200, while aerosolized drug substance is inhaled by the patient as shown by arrow 320 and air incoming into flow channel 300, driven by patient's inhalation, is shown by arrow 310.

The piercing of apertures in container 110 can be performed immediately before drug substance delivery to the patient. In one embodiment, the invention operates as follows: the inhaler is activated for use, apertures in the drug container are pierced either simultaneously or sequentially by piercing means 400, or lidding material 630 in case of tape-based drug packs 610 is removed or sheared, or tape-based pouch 710 is opened, and then drug substance 120 is aerosolized as the patient is inhaling through the inhaler. In other embodiments, the opening or piercing of individual drug packs occurs automatically upon inhalation of the patient, through electromechanical or mechanical means, such as spring or electromagnetic actuator, or thermal porator, all optionally activated by inhalation detecting sensor 420.

Figure 10:
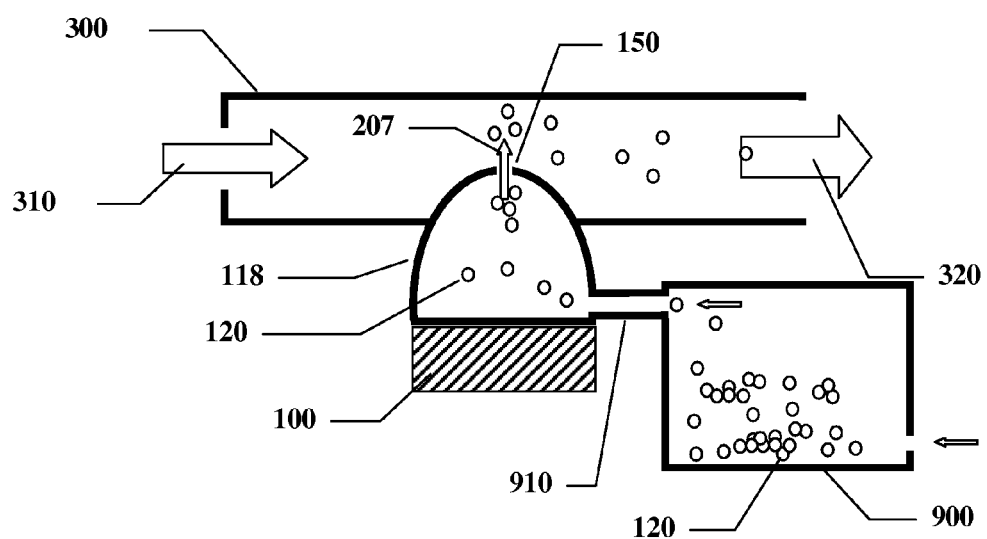
FIG. 10 is a cross-sectional view of an embodiment of the present invention showing an inhalation device.

In another embodiment, as illustrated in FIG. 10, multi-use container 118 is utilized to deliver drug substance 120, whereby side wall aperture 200 is connected to a source of drug substance 900 via a conduit 910. Source of drug substance 900 has at least two or more doses of drug substance 120. Quantity of drug substance 120 delivered to a patient is controlled by the timing of the actuation of the device, or by a sensor detecting actual quantity of delivered drug substance 120 and controlling actuation of vibrator 100.

Other embodiments and applications of the invention are contemplated. Drug substance for the delivery to the patient can be a vaccine, DNA or RNA fragment, medication for treatment of pain, asthma, emphysema, chronic bronchitis, cystic fibrosis, COPD, diabetes treatment, or any other medication capable of preventing or treating a disease or reliving symptoms of a disease when delivered in the aerosolized form to the patient and having localized and/or systemic effect.

In another embodiment, the present invention is used to deliver aerosolized drug not for inhalation but for intranasal delivery, oral delivery, eye delivery, or skin surface delivery. In another embodiment, a liquid drug formulation is delivered using the present invention.

EXAMPLE 1

A model inhaler device similar to the designs shown in FIG. 7A, capable of working with either blisters having only drug ejection apertures or both drug ejection apertures and side wall apertures, was utilized in experimental testing. The device had integrated electronics and a removable flow channel. A piezo actuator based on a modified air transducer manufactured by Murata Electronics, Japan was used as a vibrator. The piezo actuator was actuated for 4 seconds and was driven 90% of the time at a frequency of 33 kHz and 10% of the time at a frequency of 34.4 kHz, switching between these frequencies at a rate of 10 Hz (duty cycle). Alternating voltage of approximately 160-200 volts generated by a flyback circuit in a step wave-form was used to actuate the piezo actuator. A blister with approximately semi-spherical top and flat bottom was utilized as a single use container containing model dry powder for aerosolization. The height of the blister was approximately 5.5 mm and the diameter of the blister chamber at the base was approximately 11 mm, with the shape of the blister similar to the shape shown in FIG. 3C. The blister was made of aluminum foil coated with polymeric layers. The top and bottom parts of the blister were thermally sealed to each other. Top (semi-spherical) part of the blister was pierced with 4 drug ejection apertures using metallic needles 320 microns in diameter, similar to FIG. 3C, where only two drug ejection apertures 150 are shown. In some experiments, side wall of the top part of the blister was pierced with at least one side wall aperture 200, similar to FIG. 3C. A needle with diameter of 240 microns was used to pierce side wall aperture. A flow of air through the flow channel of the device was established at 30 liters per minute (LPM) using a vacuum pump. The blister was filled with variable quantities of a model dry powder, and testing of the gravimetric clearance from the blister was performed under varying experimental conditions.

The experimental results are presented in Table 1. As can be seen from Table 1, unexpected results were obtained, wherein presence of one or more side wall apertures resulted in a significant increase in the speed of drug ejection and also in the quantity of powder that can be effectively ejected, compared with conditions without side wall apertures. Comparison of tests 1 and 2; 2 and 2a; 3 and 3a; 7 and 7a; 9 and 9a indicates that side wall aperture resulted in very significant increase in clearance of the powder from the blister, when compared, at the same conditions, with blisters without side wall apertures. Also comparison of tests 4 and 4a; 5 and 5a; 6 and 6a indicates that without piezo actuation, no appreciable clearance was detected even when side wall apertures were present. Side wall apertures enabled very high gravimetric clearance of regular quantities of powder from the blister, i.e. quantities of the order of 3-6 mg, but also very large quantities of powder, for instance of the order of 15-20 mg and as high as 37 mg, wherein practically no powder ejection can be observed from blisters under same conditions without side wall apertures, as demonstrated by tests 3 and 3a; 7 and 7a; and 8 and 9a. It was visually detected that the clearance of the blisters with side wall apertures occurred fast, sometimes in less than a second, and faster vs. blisters without side wall apertures, which have not completely cleared even in 4 seconds. It was not seen that any appreciable amount of powder was ejected from side wall apertures during the testing performed.

TABLE 1

| ## | Powder in the blister, mg | Apertures in blister | Dosing Procedure | Powder cleared from blister, mg | Gravimetric Clearance % | Test conditions |
|---|---|---|---|---|---|---|
| 1* | 5.037 | 4 drug ejection apertures & side wall aperture pierced | Piezo actuated, Vacuum pump actuated | 4.807 | 95.4% | Blister with side wall aperture actuated with piezo |
| 2 | 4.204 | 4 drug ejection apertures pierced | Piezo actuated, Vacuum pump actuated | 1.035 | 24.6% | Blister without side wall aperture actuated with piezo |
| 2a** | 3.169 | 2 side wall apertures and 4 drug ejection apertures pierced | Piezo actuated, Vacuum pump actuated | 3.061 | 96.6% | Blister #2 repeated after 2 side wall apertures pierced |
| 3 | 19.028 | 4 drug ejection apertures pierced | Piezo actuated, Vacuum pump actuated | 1.051 | 5.5% | Blister without side wall aperture actuated with piezo |
| 3a* | 17.977 | Side wall aperture and 4 drug ejection apertures pierced | Piezo actuated, Vacuum pump actuated | 17.903 | 99.6% | Blister #3 repeated with side wall aperture |
| 4* | 12.215 | Side wall aperture and 4 drug ejection apertures pierced | Vacuum pump actuated for 20 seconds | 0.634 | 5.2% | Blister with side wall aperture exposed to pump air flow for 20 s; no piezo actuation |
| 4a* | 11.581 | Side wall aperture and 4 drug ejection apertures pierced | Piezo actuated, Vacuum pump actuated | 11.483 | 99.2% | Blister #4 repeated with piezo actuation |
| 5* | 7.388 | Side wall aperture and 4 drug ejection apertures pierced | Vacuum pump actuated for 20 seconds | 0.072 | 1.0% | Blister with side wall aperture exposed to air flow for 20 s; no piezo actuation |
| 5a* | 7.316 | Side wall aperture and 4 drug ejection apertures pierced | Piezo actuated, Vacuum pump actuated | 7.22 | 98.7% | Blister #5 (with side wall aperture) repeated with piezo actuation |

TABLE 1-continued

| ## | Powder in the blister, mg | Apertures in blister | Dosing Procedure | Powder cleared from blister, mg | Gravimetric Clearance % | Test conditions |
|---|---|---|---|---|---|---|
| 6* | 5.147 | Side wall aperture and 4 drug ejection apertures pierced | Vacuum pump actuated for 20 seconds | 0.025 | 0.5% | Blister with side wall aperture exposed to air flow for 20 s; no piezo actuation |
| 6a* | 5.122 | Side wall aperture and 4 drug ejection apertures pierced | Piezo actuated, Vacuum pump actuated | 5.015 | 97.9% | Blister #6 (with side wall aperture) repeated with piezo actuation |
| 7 | 17.139 | 4 drug ejection apertures pierced | Piezo actuated, Vacuum pump actuated | 1.67 | 9.7% | Blister without side wall aperture actuated with piezo |
| 7a* | 15.469 | Side wall aperture and 4 drug ejection apertures pierced | Piezo actuated, Vacuum pump actuated | 14.482 | 93.6% | Blister #7 repeated with side wall aperture |
| 8* | 23.949 | Side wall aperture and 4 drug ejection apertures pierced | Piezo actuated, Vacuum pump actuated | 23.636 | 98.7% | Blister with side wall aperture actuated with piezo |
| 9 | 37.582 | 4 drug ejection apertures pierced | Piezo actuated, Vacuum pump actuated | 0.229 | 0.6% | Blister without side wall aperture actuated with piezo |
| 9a* | 37.353 | Side wall aperture and 4 drug ejection apertures pierced | Piezo actuated, Vacuum pump actuated | 37.105 | 99.3% | Blister #9 repeated with side wall aperture |

*Tests with at least one Side Wall Aperture

EXAMPLE 2

Experimental testing was performed using an experimental setup similar to the setup described in Example 1, but with a proprietary piezo actuator G9 tuned to resonant frequency of 34.5 kHz, driven 90% of the time at a frequency of 34 kHz and 10% of the time at a frequency of 35 kHz, switching between these frequencies at rate of 10 Hz (duty cycle). Alternating voltage of approximately 160-200 volts generated by a flyback circuit in a step wave-form was used to actuate the piezo actuator. A model drug powder (insulin) was used, and demonstrated a very good clearance from the blister. In the experiment, a quantity of drug powder considerably larger vs. typical quantities of 1-3 mg per blister was used. In two tests a blister containing 5 mg of drug powder and having a side wall aperture, in addition to four drug ejection apertures demonstrated 94.6% and 95.9% clearance of powder from the blister during piezo actuation time of 4 seconds. It was observed that the actual clearance time was lower than 4 seconds of piezo actuation time. Thus unexpectedly, much larger quantity of powder is cleared from the blister having a side wall aperture vs. typically seen with the same blisters but without side wall aperture, which achieved clearances of around 80 to 95% only when filled with much lower quantities of insulin, i.e. up to about 2 mg.

EXAMPLE 3

Using an experimental setup similar to the setup described in Example 2, a test of a model drug powder blend with lactose was performed with very good clearance, wherein 6 mg of the blend cleared with 97.5% gravimetric clearance from a blister having a side wall aperture. The same blisters but without side wall aperture, demonstrated much lower gravimetric clearances.

EXAMPLE 4

Figure 3:
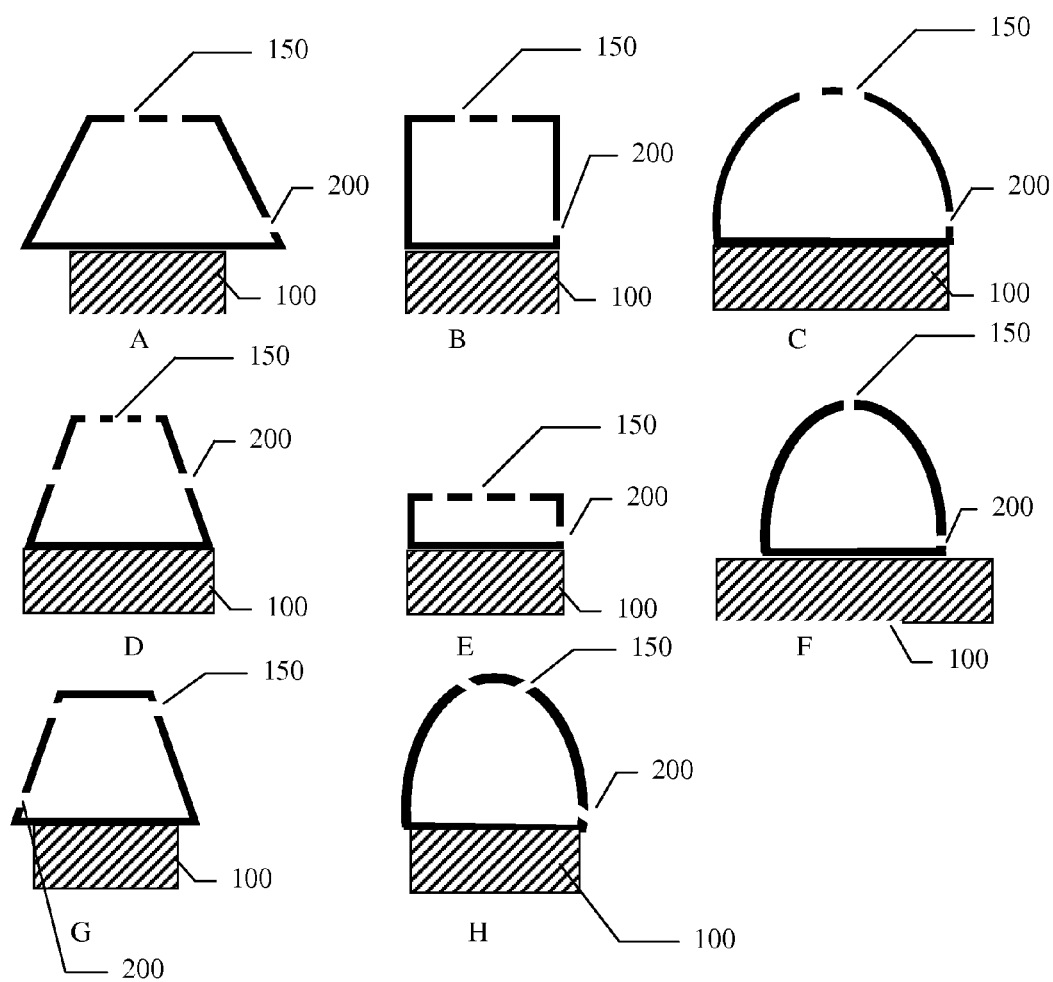
FIG. 3 is a cross-sectional view of several embodiments of the present invention showing containers with a drug substance coupled to vibrators.
Figure 4:
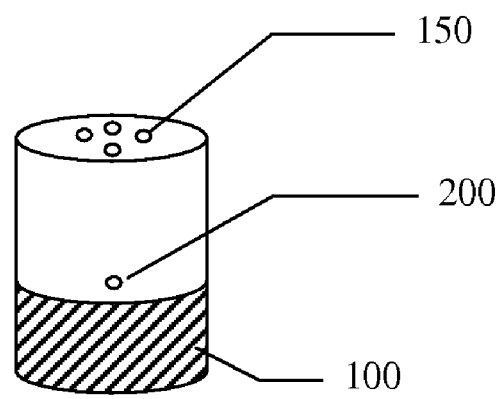
FIG. 4 is a cross-sectional view of an embodiment of the present invention showing a container with a drug substance coupled to a vibrator.
Figure 5:
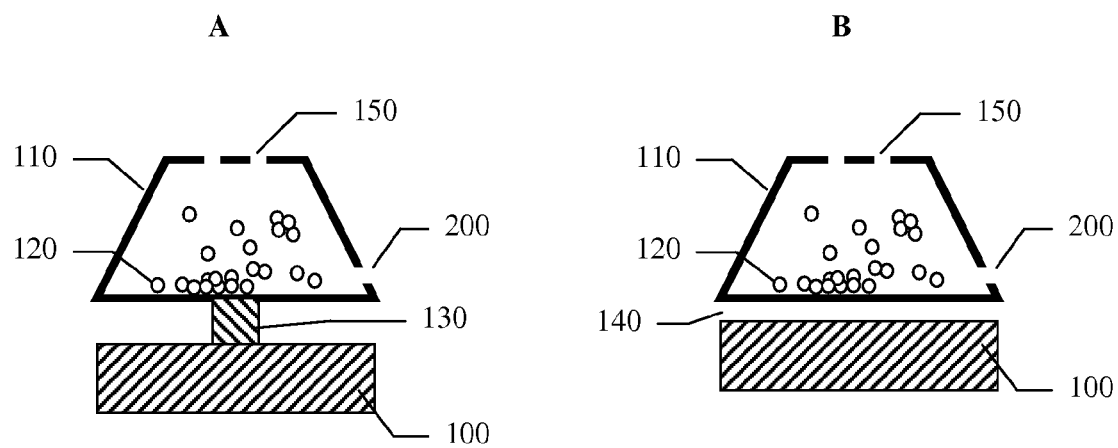
FIG. 5 is a cross-sectional view of several embodiments of the present invention showing containers with a drug substance coupled to vibrators.

Experiments were performed in a setup similar to the experimental setup described in Example 1, but with a non-modified Murata Electronics air transducer serving as a piezo actuator, having resonant frequency of 40 kHz. Piezo actuators with other resonant frequencies can also be used, typically in the range from 30 to 45 kHz. Flow of air through the device was established at 28 LPM using a vacuum pump. Plastic cone-shaped top and cone-shaped, flat top blisters with flat metal foil bottom were utilized as single use containers containing model powder for aerosolization, similar to the blisters depicted in correspondingly FIGS. 3F and 3D. The blisters with cone shaped top had straight cone top, while cone-shaped, flat top blisters had a cone top coming to a flat end with the diameter of approximately 2 mm. The height of the blisters was approximately 4.5 mm and the diameter of the blister chamber at the base was approximately 8 mm. Blister tops were made by thermoforming of PVC or PETG plastic and thermally sealed to the blister bottom, made of polymer-clad aluminum foil. The top part of the blisters was pierced with 3 holes using metallic needles 240 microns in diameter, thus forming drug ejection apertures, similar to FIG. 3D. In some experiments, the side wall of the conical part of the blister was pierced with at least one side wall aperture, similar to FIGS. 3A, 3B, 3C. A needle with a diameter of 240 microns was used to pierce the side wall aperture. The results of these experiments are presented in Table 2.

TABLE 2

| ## | Blister Shape | Powder in the blister, mg | Piezo actuation time | Powder cleared from blister, mg | Gravimetric Clearance % | Test conditions |
|---|---|---|---|---|---|---|
| 10* | cone shaped | 4.006 | 4 sec | 3.902 | 97.4% | Side Wall Aperture |
| 11* | cone shaped | 5.514 | 4 sec | 5.454 | 98.9% | Side Wall Aperture |

TABLE 2-continued

| ## | Blister Shape | Powder in the blister, mg | Piezo actuation time | Powder cleared from blister, mg | Gravimetric Clearance % | Test conditions |
|---|---|---|---|---|---|---|
| 12 | cone shaped | 3.764 | 4 sec | 2.516 | 66.8% | No Side Wall Aperture |
| 13* | Cone shaped flat top | 6.769 | 2 sec | 6.617 | 97.8% | Side Wall Aperture |
| 14 | Cone shaped flat top | 3.194 | 2 sec | 2.984 | 93.4% | No Side Wall Aperture |

*Tests with at least one Side Wall Aperture

As can be seen from the Table 2, unexpected results were obtained, wherein a significant increase in the speed of powder ejection and also quantity of powder that can be ejected form a blister was experimentally observed, compared with conditions without side wall apertures.

EXAMPLE 5

Testing of the air flow in and out of the blister having several drug ejection apertures and at least one side wall aperture was performed. Experimental setup was similar to the setup described in Example 1, but no powder was present in the blisters in these experiments and no air flow was established using a vacuum pump. In addition, a plastic capillary tubing was connected to the side wall aperture from outside. In the first test, when the blister was intermittently actuated with the piezo actuator, a sensitive lightweight flag was observed moving towards the inlet of the plastic capillary tubing thus registering the vacuum and/or air flow through the capillary tubing and through side wall aperture into the blister, while air is being ejected from the drug ejection apertures on top of the blister.

In the second test, a second lightweight flag was placed above drug ejection apertures on top of the blister, said lightweight flag was observed moving upwards detecting jets of air emanating from drug ejection apertures. At the same time the first sensitive lightweight flag was observed moving towards the inlet of the plastic capillary tubing thus registering the vacuum and/or air flow through the capillary tubing and through the side wall aperture into the blister, said first flag being suctioned to the plastic capillary tubing inlet and blocking it. It was further observed that when said first flag was manually removed from blocking the plastic capillary tubing inlet and thus from blocking the air intake into the side wall aperture, the second flag indicated notable increase in air jets emitted from the drug ejection apertures on top of the blister. Thus is appears that side wall aperture helped increasing the jetting of air emanating from the blister by providing air supply into the blister.

EXAMPLE 6

Experiments were performed in a setup similar to the experimental setup described in Example 2, but without activating a vacuum pump and driving any air through the flow channel of the experimental setup. A model lactose dry powder was used in the experiments. In a blister without the side wall aperture, filled with 6.390 mg of lactose, a clearance of only 28.4% was observed. In blisters with side aperture, filled with 5.013 and 6.560 mg of lactose powder, a clearance of correspondingly 80.8% and 93.4% was observed. Thus unexpected results were obtained, wherein a significant increase in the speed of powder ejection and also quantity of powder that can be ejected was experimentally observed, compared with conditions without side wall apertures.

While the present invention has been particularly described, in conjunction with specific preferred embodiments, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

We claim:

1. An dry powder inhaler, comprising:
    an inhaler body including a space for accommodating a container containing a dry powder, a vibratory element, a flow channel, and electronic circuitry to electrically drive the vibratory element, wherein said container has a flat bottom wall, a top wall and a side wall bridging the top wall and the bottom wall;
    at least one drug substance ejection aperture in the top wall of said container; and
    at least one air intake aperture in the side wall of said container;
    wherein said vibratory element has a flat surface adapted to couple to the flat bottom of said container to vibrate said container and to eject said drug substance from said container through said at least one drug substance ejection aperture and into said flow channel adapted to be inhaled by a patient.

2. The inhaler as in claim 1, wherein said drug substance is deaggregated and aerosolized when ejected from said container.

3. The inhaler as in claim 1, wherein said drug substance is ejected from said container through synthetic jetting.

4. The inhaler as in claim 1, wherein said container is sized to empty of said drug substance in less than approximately 2 seconds.

5. The inhaler as in claim 1, wherein said drug substance is ejected from said container with gravimetric clearance from approximately 80% of said drug substance to approximately 100% of said drug substance.

6. The inhaler as in claim 1, wherein said drug substance is present in said container in quantity from approximately 1 mg to approximately 100 mg.

7. The inhaler as in claim 1, wherein said drug substance is selected from the group consisting of a drug powder, a mixture of a drug powder with an excipient, a mixture of two or more pharmaceutically active drug powder materials, a mixture of two or more pharmaceutically active drug powder materials with an excipient, and a combination thereof.

8. The inhaler as in claim 1, wherein said at least one air intake aperture is round and has a diameter from about 25 microns to about 400 microns.

9. The inhaler as in claim 1, wherein said at least one air intake aperture is round, triangular, square, or polygonal in shape.

10. The inhaler as in claim 1, wherein said container comprises a foil blister, a foil pouch, a plastic blister, or a combination thereof.

11. The inhaler as in claim 1, wherein said container is reusable.

12. The inhaler as in claim 1, wherein said container is formed from a metal, a metal foil, a polymer-coated metal foil, a polymer film, a barrier coated polymer film, a polymer, a polymer laminate, and a combination thereof.

13. The inhaler as in claim 1, wherein said vibratory element is a piezo actuator, a piezo transducer, or a piezo vibrator.

14. The inhaler as in claim 1, further comprising a driver for driving said vibratory element to vibrate at ultrasonic frequencies.

15. The inhaler as in claim 1, wherein said container has one air intake aperture and four drug substance ejection apertures.

16. The inhaler as in claim 1, having at least two apertures in the top wall of the container.

17. The inhaler as in claim 1, wherein said at least one aperture in the top wall of the container is in communication with an air stream in said flow channel adapted to be inhaled by a patient,
wherein upon vibrating said drug is ejected from said at least one aperture in the top wall and picked up by said air stream adapted to be inhaled by said patient.

18. The inhaler as in claim 1, wherein the total area of ejection aperture(s) in the top wall of the container is at least two times the total area of our intake aperture(s) in the side wall(s) of the container.

19. The inhaler as in claim 18, wherein the total area of ejection aperture(s) in the top wall of the container is at least five times the total area of air intake aperture(s) in the side wall(s) of the container.

* * * * *